US009267164B2

(12) United States Patent
O'Keefe

(10) Patent No.: US 9,267,164 B2
(45) Date of Patent: Feb. 23, 2016

(54) METHOD OF RECOMBINANT MACROMOLECULAR PRODUCTION

(75) Inventor: Donald O'Keefe, Doylestown, PA (US)

(73) Assignee: Da Yu Enterprises, L.L.C., Yardley, PA (US)

( * ) Notice: Subject to any disclaimer, the term of this patent is extended or adjusted under 35 U.S.C. 154(b) by 0 days.

(21) Appl. No.: 13/825,895

(22) PCT Filed: Sep. 23, 2011

(86) PCT No.: PCT/US2011/052911
§ 371 (c)(1),
(2), (4) Date: Mar. 25, 2013

(87) PCT Pub. No.: WO2012/040550
PCT Pub. Date: Mar. 29, 2012

(65) Prior Publication Data
US 2013/0183685 A1    Jul. 18, 2013

Related U.S. Application Data

(60) Provisional application No. 61/386,513, filed on Sep. 26, 2010.

(51) Int. Cl.
| | |
|---|---|
| *C12P 21/06* | (2006.01) |
| *C12Q 1/02* | (2006.01) |
| *C12N 1/06* | (2006.01) |
| *C12P 21/02* | (2006.01) |
| *G01N 33/50* | (2006.01) |
| *C07H 21/02* | (2006.01) |
| *C07H 21/04* | (2006.01) |
| *C12N 15/00* | (2006.01) |
| *C12N 5/00* | (2006.01) |
| *C12N 5/10* | (2006.01) |
| *C12P 21/04* | (2006.01) |
| *C12Q 1/68* | (2006.01) |

(52) U.S. Cl.
CPC ............... *C12Q 1/025* (2013.01); *C12N 1/066* (2013.01); *C12P 21/02* (2013.01); *G01N 33/5005* (2013.01); *G01N 2500/10* (2013.01)

(58) Field of Classification Search
None
See application file for complete search history.

(56) References Cited

U.S. PATENT DOCUMENTS

| | | | | | |
|---|---|---|---|---|---|
| 4,209,331 | A | * | 6/1980 | Kukanskis et al. | 106/1.23 |
| 6,512,166 | B1 | * | 1/2003 | Harman et al. | 800/301 |
| 7,256,005 | B2 | * | 8/2007 | Zitzmann et al. | 435/7.2 |
| 7,312,060 | B2 | * | 12/2007 | Rothschild et al. | 435/194 |
| 7,608,275 | B2 | * | 10/2009 | Deem et al. | 424/236.1 |
| 2003/0086919 | A1 | * | 5/2003 | Rosenblum et al. | 424/94.63 |
| 2003/0186337 | A1 | * | 10/2003 | Girard et al. | 435/7.23 |
| 2003/0203360 | A1 | * | 10/2003 | Weinstein et al. | 435/6 |
| 2006/0110766 | A1 | * | 5/2006 | Robertson et al. | 435/6 |
| 2008/0026418 | A1 | * | 1/2008 | Black et al. | 435/32 |
| 2008/0268472 | A1 | * | 10/2008 | Brown et al. | 435/7.21 |
| 2008/0280781 | A1 | * | 11/2008 | Chen et al. | 506/14 |
| 2008/0286750 | A1 | * | 11/2008 | Xu et al. | 435/4 |
| 2009/0136914 | A1 | * | 5/2009 | Ramadugu et al. | 435/5 |
| 2010/0196345 | A1 | * | 8/2010 | Shaaltiel et al. | 424/94.61 |

FOREIGN PATENT DOCUMENTS

WO    WO 2006/076742    7/2006

OTHER PUBLICATIONS

O'Keefe et al., "Cloned diphtheria toxin within the periplasm of *Eschericia coli* causes lethal membrane damage at low pH" 86 Proceedings of the National Academy of Sciences USA 343-346 (1989).*

Dicker et al., "Control of membrane permeability by external and internal ATP in 3T6 cells grown in serum-free medium" 77(4) Proceedings of the National Academy of Sciences USA 2103-2107 (1980).*

Rozengurt et al., "Effect of Exogenous ATP on the Permeability Properties of Transformed Cultures of Mouse Cell Lines" 252(13) The Journal of Biological Chemistry 4584-4590 (1977).*

Gennis, "The Concept of an Energized Membrane" Biomembranes Molecular Structure and Function pp. 264-265 (Springer-Verlag New York ed. Robert B. Gennis (1989).*

Fernandez et al, "Specific secretion of active single chain Fv antibodies into the supernatants of *Escherichia coli* cultures by use of the hemolysin system", Applied and Environmental Microbiology, 66(11):5024-9 (Nov. 2000).

Giacalone et al, "Toxic protein expression in *Escherichia coli* using a rhamnose-based tightly regulated and tunable promoter system" Biotechniques, 40(3):355-64 (Mar. 2006).

O'Keefe et al, "pH-dependent insertion of proteins into membranes: B-chain mutation of diphtheria toxin that inhibits membrane translocation", Glu-349→Lys., PNAS, 89(13):6202-6 (Jul. 1, 1992).

Davidson et al, "Dependence of the Activity of Colicin E 1 in Artificial Membrane Vesicles on pH, Membrane Potential, and Vesicle Size", Journal Biological Chemistry, 259(1):594-600 (Jan. 1984).

Nguyen, "Three- dimensional model of the pore form of Anthrax protective antigen. Structure and biological implications", J. Biomol. Stract. Dynam., vol. 22(3) pp. 253-265 (Dec. 2004).

(Continued)

*Primary Examiner* — Nancy J Leith
(74) *Attorney, Agent, or Firm* — Howson & Howson LLP

(57) ABSTRACT

A method for recombinantly expressing a macromolecule in a host cell is disclosed which involves culturing a host cell which contains two nucleic acid sequences, i.e., a first nucleic acid sequence encoding a membrane-permeabilizing agent and a second nucleic acid sequence encoding a desired macromolecule under the operative control of an inducible promoter, to a selected cell density that permits accumulation of the agent. Thereafter the host cell is exposed to an environmental condition that induces the agent to disrupt the integrity of the cell membrane without complete lysis of the cell membrane. The host cell thereby allows transport through the membrane of small molecular weight compounds. These resulting host cells are cultured in the presence of a nutrient cocktail that contains components that can transport through the disrupted cell membrane, e.g., an inducing agent that induces the tightly regulated promoter and metabolic requirements that permit expression of the macromolecule.

19 Claims, No Drawings

(56) References Cited

OTHER PUBLICATIONS

Walker, et al., "Key residues for membrane binding, oligomerization, and pore forming activity of staphylococcal alpha-hemolysin identified by cysteine scanning mutagenesis and targeted chemical modification", J. Biol. Chem., vol. 270 (39) pp. 23065-23071 (Sep. 1995).

Movileanu et al., "Location of a constriction in the lumen of a transmembrane pore by targeted covalent attachment of polymer molecules", J. Gen. Phsyiol., vol. 117(3) pp. 239-252 (Mar. 2001).

Mourez et al., "Mapping dominant-negative mutations of anthrax protective antigen by scanning mutagenesis", PNAS, vol. 100(24) pp. 13803-13808 (Nov. 2003).

Nassi et al., "PA63 channel of anthrax toxin: an extended beta-barrel", Biochemistry, vol. 41(5) pp. 1445-1450 (Feb. 2002).

Song et al., "Structure of staphylococcal alpha-hemolysin, a heptameric transmembrane pore", Science, vol. 274(5294) pp. 1859-1866 (Dec. 1996).

Sun et al., "Phenylalanine-427 of anthrax protective antigen functions in both pore formation and protein translocation", PNAS, vol. 105(11) pp. 4346-4351 (Mar. 2008).

International Search Report and Written Opinion mailed Jan. 18, 2012 in corresponding International Patent Application No. PCT/US11/052911.

Examination Report dated Feb. 21, 2014 issued in corresponding Australian Patent Application No. 2011305249.

First Office Action dated Mar. 5, 2014 issued in corresponding Chinese Patent Application No. 201180046332.8.

Office Action dated Jul. 23, 2014 issued in corresponding Japanese Patent Application No. 2013-530345.

Applicant's instructions to agent regarding response dated Oct. 10, 2014, with confidential information redacted.

Office Action dated Nov. 15, 2014 issued in corresponding Chinese Patent Application No. 201180046332.8.

Office Action dated Oct. 30, 2014 issued in corresponding Canadian Patent Application No. 2811297.

Finean et al. Membranes and their Cellular Functions (3$^{rd}$ Ed) (Chp 4). pp. 77-103. Blackwell Scientific Publications: London. Jan. 1, 1984.

Farid-Sabet. Colicins and Bacterial Membranes: Structures and Functions. The Journal of Biological Chemistry. vol. 253(3):990-995. Feb. 10, 1978.

Morth et al. A structural overview of the plasma membrane Na+, K+-ATPase and H+-ATPase ion pumps. Nature Reviews—Molecular Cell Biology. vol. 12:60-70. Jan. 2011.

Harvey et al. Animal Plasma Membrane Energization by Chemiosmotic H+ V-ATPases. The Journal of Experimental Biology. vol. 200(2):203-213. Jan. 15, 1997.

White. The Physiology and Biochemistry of Prokaryotes (2$^{nd}$ Ed)(Chp 3). pp. 66-103. Oxford University Press: Oxford. Jan. 1, 2000.

Stearns et al. The Proton Motive Force from Microbiology for Dummies. Dummies.com, accessed on Mar. 12, 2015 from http://www.dummies.com/how-to-content/the-proton-motive-force.html.

Bush. Antimicrobial agents targeting bacterial cell walls and cell membranes. Scientific and Technical Review of the Office International des Epizooties (Paris). vol. 31(1):43-56. Apr. 2012.

Ruhr et al. Mode of Action of the Peptide Antibiotic Nisin and Influence on the Membrane Potential of Whole Cells and on Cytoplasmic and Artificial Membrane Vesicles. Antimicrobial Agents and Chemotherapy. vol. 27(5):841-845. May 1985.

Ohsuka et al. Lidocaine Hydrochloride and Acetylsalicylate Kill Bacteria by Disrupting the Bacterial Membrane Potential in Different Ways. Microbiol. immunol. vol. 38(6):429-434. Jan. 1994.

Smarda. Colicin K Decreases the Density of Intramembrane Particles (IMP) in the Cell Membrane of *Escherichia coli*. Journal of General Microbiology. vol. 134:1283-1288. Aug. 1987.

Montville et al. Evidence that dissipation of proton motive force is a common mechanism of action for bacteriocins and other antimicrobial proteins. International Journal of Food Microbiology. vol. 24(102):53-74. Dec. 1994.

Dankert et al. Bacterial killing by complement—C9-mediated killing in the absence of C5b-8. Biochem. J. vol. 244(2):393-399. Jun. 1, 1987.

De La Peña et al. Effect of Yeast Killer Toxin on Sensitive Cells of *Saccharomyces cerevisiae*. The Journal of Biological Chemistry. vol. 256(20):10420-10425. Oct. 25, 1981.

Sahl. Influence of the Staphylococcinlike Peptide Pep 5 on Membrane Potential of Bacterial Cells and Cytoplasmic Membrane Vesicles. Journal of Bacteriology. vol. 162(2):833-836. May 1985.

Solini et al. Human primary fibroblasts in vitro express a purinergic P2X7 receptor coupled to ion fluxes, microvesicle formation and IL-6 release. Journal of Cell Science. vol. 112:297-305. Jan. 1999.

Di Virgilio et al. Cytolytic P2X purinoceptors. Cell Death and Differentiation. vol. 5:191-199. Oct. 22, 1997.

Pelegrin et al. The P2X7 receptor-pannexin connection to dye uptake and IL-1B release. Purinergic Signalling. vol. 5:129-137. Feb. 2009.

Gonzalez et al. Extracellular ATP induces the release of calcium from intracellular stores without the activation of protein kinase C in Swiss 3T6 mouse fibroblasts. PNAS. vol. 86:4530-4534. Jun. 1989.

Suprenant et al. Signaling at Purinergic P2X Receptors. Annu Rev. Physiol. vol. 71:333-359. Oct. 13, 2008.

MacKenzie et al. Pseudoapoptosis Induced by Brief Activation of ATP-gated P2X7 Receptors. The Journal of Biological Chemistry. vol. 280(40):33968-33976. Oct. 7, 2005.

Freedman et al. Evidence for Voltage Modulation of IL-2 Production in Mitogen-Stimulated Human Peripheral Blood Lymphocytes. The Journal of Immunology. vol. 149:3784-3794. Dec. 15, 1992.

Applicant's correspondence to agent dated Jan. 19, 2015 providing instructions for response to Office Action dated Nov. 15, 2014 issued in corresponding Chinese Patent Application No. 201180046332.8.

Applicant's response dated Apr. 15, 2015 to Office Action dated Oct. 30, 2014 issued in corresponding Canadian Patent Application No. 2811297.

Hsiung, H.M. et al., Use of Bacteria Release Protein in *E. Coli* for Excretion of Human Growth Hormone into the Culture Medium, Biotechnology, Mar. 1989, 7(3):267-271.

Liu, Y. et al., Preparation of High-Activity Whole Cell Biocatalysts by Permeabilization of Recombinant Yeasts with Alcohol, Journal of Bioscience and Engineering, Jun. 2000, 89(6):554-558.

Schwaneberg, U. et al., Cost-Effective Whole-Cell Assay for Laboratory Evolution of Hydroxylases in *Escherichia Coli*, Journal of Biomolecular Screening, Apr. 2001, 6(2):111-117.

Xu, L. et al., Heat-Inducible Autolytic Vector for High-Throughput Screening, Biotechniques, Sep. 2006, 41(3):319-322.

Chen, R., Permeability Issues in Whole-Cell Bioprocesses and Cellular Membrane Engineering, Applied Microbiology and Biotechnology, Jan. 2007, 74(4):730-738.

Spexard, M. et al., Screening for Conditions of Enhanced Production of a Recombinant beta-glucanase secreted into the medium by *Escherichia coli*, Biotechnology Letters, Oct. 2009, 32(2):243-248.

Extended European Search Report dated Nov. 18, 2015, including the supplementary European search report and the European search opinion, in corresponding European Application No. 11827591.6, filed Apr. 12, 2013.

* cited by examiner

METHOD OF RECOMBINANT MACROMOLECULAR PRODUCTION

CROSS-REFERENCE TO RELATED APPLICATIONS

This application is a national stage of International Patent Application No. PCT/US2011/052911, filed Sep. 23, 2011, which claims the benefit of the priority of U.S. Provisional Patent Application No. 61/386,513, filed Sep. 26, 2010, which applications are incorporated herein by reference.

BACKGROUND OF THE INVENTION

Recombinant macromolecules are of considerable interest to pharmaceutical and biotechnological research and include both nucleic acids (ribo- and deoxyribonucleic acids) and proteins. Of these, recombinant proteins receive the most attention due to their diversity and numerous applications. Certain aspects of pharmaceutical and biotechnological research are dependent upon the production of recombinant macromolecules. Such recombinant macromolecules are produced in a variety of host cells including, but not limited to, bacterial cells (e.g., *Escherichia coli*), yeast cells, insect cells, and mammalian cells. In many instances, the recombinant macromolecule is produced in a heterologous host cell, i.e., a host cell that is different from the macromolecule's native source. For example, the biotechnology drug human growth hormone, which is a secreted protein from the human pituitary gland, is produced recombinantly in the bacterium *Escherichia coli* (*E. coli*). Such heterologous host cell systems do not always successfully produce the desired recombinant macromolecule. Often times the desired protein can be misfolded in the heterologous host cell (i.e., it does not have its native structure and is therefore nonfunctional), or expressed in a form that is insoluble, toxic, aggregated, or degraded. Often the recombinant macromolecule is simply produced in insufficient quantities in the heterologous host cell. Modified recombinant proteins or recombinant fusion proteins may also pose production challenges, even in homologous host cell systems, due to their unnatural compositions.

A common approach to address the above-noted challenges of recombinant macromolecule production is the use of alternative host cell systems. However, certain macromolecular production problems, such as misfolded proteins, are addressed post production in the host cell system, which can be labor intensive as well as not being effective for all proteins. In addition, addressing these issues is generally a protein specific process, resulting in low throughput. Another method to address certain macromolecular production problems involves the use of cell-free protein expression systems. A practical limitation of these systems is that they are not scaleable. The protein production limit of cell-free expression systems is generally 50 milligrams or less, and often the production limit is just a few milligrams. In addition, storage of the cell extracts and cell lysates leads to a diminution in their capacity to produce protein. These systems also have no meaningful capacity to produce significant amounts of nucleic acid and therefore require a second system to provide a supply of the requisite DNA template.

SUMMARY OF THE INVENTION

In one aspect, a method for recombinantly expressing a macromolecule in a host cell is provided. This method comprises culturing a host cell which contains a nucleic acid sequence encoding a membrane-permeabilizing agent and a nucleic acid sequence encoding a desired macromolecule, both sequences under the control of separate regulatory sequences, until a suitable cell density is reached. During this step, the membrane-permeabilizing agent has been produced within the cell. In one aspect, the method involves exposing the host cell to an environmental condition that induces the membrane-permeabilizing agent to disrupt the integrity of the cell membrane without complete lysis of the cell membrane. Thereafter, the cell is provided with a nutrient cocktail containing small molecular weight components that can transport through the disrupted cell membrane. These components can include an inducing agent that induces a promoter directing expression of the macromolecule, and sufficient metabolic requirements that permit expression of the macromolecule in the membrane-disrupted host cell. This method allows the macromolecule to be expressed in the correct conformation and/or in a desired amount within the host cell. In certain embodiments, the cells are concentrated prior to any inducing environmental condition and contact with the nutrient cocktail. In other embodiments, the cells, after contact with the nutrient cocktail and induction of expression of the macromolecule, are lysed and the macromolecule harvested.

In another aspect, a method for enhancing recombinant expression of a macromolecule in a host cell is provided. This method involves contacting a host cell containing a nucleic acid sequence encoding a macromolecule under the control of a tightly regulated promoter, which cells have reached a suitable cell density, with a membrane-permeabilizing agent. The agent is applied to the cell culture externally and disrupts the integrity of the cell membrane without complete lysis of the membrane. Thereafter the cell is provided with a nutrient cocktail containing small molecule weight components that can transport through the disrupted cell membrane. These components can include an inducing agent that induces the promoter directing expression of the macromolecule and sufficient metabolic requirements that permit expression of the macromolecule in the membrane-disrupted host cell. This method allows the macromolecule to be expressed in the correct conformation and/or in a desired amount within the host cell. In certain embodiments, the cells are concentrated prior to contact with the membrane-permeabilizing agent and the nutrient cocktail. In other embodiments, the cells, after contact with the nutrient cocktail and induction of expression of the macromolecule, are lysed and the macromolecule harvested.

In still another aspect, a method for in situ drug screening involves use of one or the other methods for recombinant production of a desired macromolecule as described above. In one aspect, the method involves culturing in each well of a mini-well plate a host cell containing both nucleic acid sequences, as described above. In one embodiment, each well contains a nucleic acid sequence encoding the same macromolecule. In another embodiment, each well contains a nucleic acid sequence encoding a different similar macromolecule, e.g., one member of a library of variant macromolecules. In another embodiment, each well contains a nucleic acid sequence encoding a different macromolecule, e.g., a genomic library. These host cells in each well are then exposed to an environmental condition suitable to induce the expression of the membrane-permeabilizing agent in the cell to disrupt the integrity of the cell membrane without complete lysis of the membrane as indicated above. In each well the host cells are cultured in the presence of the above-described nutrient cocktail, resulting in expression of the macromolecules in the host cells of each well. In one embodiment in which each well contains the same expressed macromolecule, a different test reagent is applied to each well. In another embodiment, in which each well expresses a different macromolecule variant or a different macromolecule, the same test reagent is applied to each well. Subsequent use of conventional assays, e.g., ELISAs, mass spectrometry, etc., permit the determination of the identity of the macromolecule that responded to the single test reagent in one embodiment, or the identity of the test reagent that induced a response in the same macromolecules, in the other aspect.

In yet another aspect, the in situ drug screening involves the use of the externally applied membrane-permeabilizing agent/macromolecule production method described above. In this aspect, the screening further involves exposing the cells in each well to externally applied membrane-permeabilizing agent, optionally with other environmental conditions. Thereafter, the test agent(s) are applied to the wells and assayed in the same manner as mentioned herein.

Other aspects and advantages of these methods are described further in the following detailed description of the preferred embodiments thereof.

DETAILED DESCRIPTION OF THE INVENTION

The present invention is a method for producing recombinant macromolecules that otherwise may be difficult to produce in host cell systems due to improper structure, toxicity, insolubility, novel constituents or insufficient quantities. The methods, described in detail below, involve treating a host cell capable of producing the desired recombinant macromolecule with a membrane-permeabilizing agent to disrupt the integrity of the host cell's membrane followed by exposing the host cell to conditions sufficient for the production of the desired recombinant macromolecule.

I. Methods of Recombinantly Producing Macromolecules

According to the methods described herein, the cellular membrane of the host cell in which a selected macromolecule is expressed is deliberately manipulated to permit the macromolecule to be expressed in large quantities and in the correct conformation.

The integrity of a cell's membrane is necessary to maintain its permeability barrier (which controls the transport of molecules to the cell's interior), its compartmentalization function (which allows the cell to maintain an internal environment different from the external environment), and its capacity for energy production (which provides the cell with an energy source for its metabolic activities). All these functions are necessary for the cell to maintain its metabolic activity, including macromolecular production. Should the integrity of the cell's membrane be sufficiently compromised, macromolecular production would stop.

The cell membrane's permeability barrier allows certain molecules to enter the cell interior through two basic mechanisms: active and passive transport. Active transport is an energy requiring process capable of transporting molecules against a concentration gradient (low to high concentration) with the aid of a selective transport complex for facilitating a specific molecule's entry to the cell interior. Such transport complexes are specific and saturable and therefore limited in their ability to deliver a diversity of molecules across the cell membrane. Passive transport, on the other hand, does not require an energy source and generally only works to transport molecules down a concentration gradient (high to low concentration). Passive transport conveys non-water molecules across cellular membranes often by one of two basic mechanisms: simple diffusion and facilitated diffusion. In simple diffusion, molecules move by random motion from a region of high concentration to a region of low concentration.

However, with the presence of a cell membrane not all molecules diffuse across the membrane equally. Restrictive criteria for simple diffusion across cell membranes can include a molecule's size, charge, or solubility. Facilitated diffusion, on the other hand, utilizes a selective complex for transferring molecules across cellular membranes down a concentration gradient.

Despite the variety of transport mechanisms extant, not all molecules have equal access to the cell's interior because of the selective permeability of the cell's membrane. According to the present methods, reducing the selectivity of a cell's membrane allows a greater diversity of molecules to diffuse across the cell's membrane into the cell interior for the purpose of enhancing expression of an inserted macromolecule expression system.

The cell membrane also allows the cell to maintain an internal environment different from the external environment. Separating these two environments allows the cell to create an optimal intracellular environment conducive to its many metabolic reactions including protein synthesis, nucleic acid synthesis, and energy generation. Specific differences in the intracellular environment versus the extracellular environment include pH, salt concentration, osmolarity, solute concentration and reduction-oxidation (redox) potential. According to the present methods, described in detail herein, disrupting the integrity of a cell's membrane allows equilibration between the cell's internal and external environments.

Finally, cell membranes can provide a potential energy source to the cell by maintaining both a pH difference across the membrane and a membrane potential (a charge difference across the membrane). When the charge difference is due to the separation of protons, the potential energy is referred to as the proton motive force. In certain cells, the proton motive force can indirectly contribute to the production of ATP, which is a critical chemical energy source for the cell. The present methods cause the membrane potential to be lost by permeabilizing the membrane, thereby cancelling the energized membrane function. The host cell's metabolic activities are thereby provided externally by the alternative energy source provided in the nutrient cocktail.

The present methods manipulate the cellular membrane permeability to enhance production of a selected macromolecule. One embodiment of the invention provides a method for recombinantly expressing a macromolecule in a host cell. The method comprises culturing to a cell density sufficient to meet the desired production levels of the macromolecule, a host cell containing a first nucleic acid sequence encoding a membrane-permeabilizing agent under the operative control of a first regulatory sequence that directs expression of the agent in the host cell; and a second nucleic acid sequence encoding the macromolecule under the operative control of a second regulatory sequence comprising a tightly regulated promoter, the second regulatory sequence directing the expression of the macromolecule in the host cell.

In this embodiment, the method exposes the host cell to an environmental condition that induces the membrane permeabilizing agent to disrupt the integrity of the cell membrane without complete lysis of the cell membrane, thereby allowing transport through the membrane of small molecular weight compounds. In this embodiment, the method includes culturing the host cell in the presence of a nutrient cocktail comprising components that can transport through the disrupted cell membrane, the components comprising an inducing agent that induces the promoter of the second regulatory sequence and metabolic requirements that permit expression of the macromolecule in the membrane-disrupted host cell.

Another aspect of the invention provides a method for enhancing recombinant expression of a macromolecule in a host cell. The method comprises contacting a host cell at a suitable cell density with a membrane-permeabilizing agent that disrupts the integrity of the cell membrane without complete lysis of the membrane, and allows transport through the membrane of small molecular weight compounds, the host cell containing a nucleic acid sequence encoding a macromolecule under the operative control of a regulatory sequence comprising a tightly regulated promoter, the regulatory sequence directing expression of the macromolecule in the host cell.

The method further comprises culturing the host cells in the presence of a nutrient cocktail comprising components that can transport through the disrupted cell membrane, the components comprising metabolic requirements that permit enhanced expression of the macromolecule in the membrane-disrupted host cell.

II. Components of the Macromolecule Production Methods

Unless defined otherwise in this specification, technical and scientific terms used herein have the same meaning as commonly understood by one of ordinary skill in the art to which this invention belongs and by reference to published texts. While various embodiments in the specification or claims are presented using "comprising" language, under various circumstances, a related embodiment may also be described using "consisting of" or "consisting essentially of" language. It is to be noted that the term "a" or "an", refers to one or more, for example, "a compound," is understood to represent one or more compounds. As such, the terms "a" (or "an"), "one or more," and "at least one" are used interchangeably herein.

A. Host Cells

By the term "host cell", it is meant a cell derived from a prokaryotic microorganism or a eukaryotic cell line cultured as a unicellular entity, which can be, or has been, used as a recipient for recombinant vectors. The term includes the progeny of the original cell which has been transfected. It is understood that the progeny of a single parental cell may not necessarily be completely identical in morphology or in genomic or total DNA complement to the original parent, due to accidental or deliberate mutation. Derivatives/progeny of the parental cell, which are sufficiently similar to the parent to be characterized by the relevant property, such as the presence of a nucleotide sequence encoding desired biosynthetic enzymes, are included in the definition, and are covered by the above terms. The appropriate host cell may be readily selected by one skilled in the art. Host cells useful in the present method include bacterial cells, yeast cells, mammalian cells, and insect cells.

Suitable host cells or cell lines useful in this method include bacterial cells. For example, the various strains of *E. coli* (e.g., HB101, MC1061, MM294, W3110, BL21 and strains used in the following examples) are well-known as host cells in the field of biotechnology. Various strains of *B. subtilis, Pseudomonas, Streptomyces*, and other bacilli and the like are also employed in this method. Mammalian cells, such as human 293 cells, Chinese hamster ovary cells (CHO), the monkey cell lines COS-1 and Vero, the myeloma cell line NSO or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. (See, e.g., Gething and Sambrook, 1981 Nature, 293:620-625, or alternatively, Kaufman et al, 1985 Mol. Cell. Biol., 5(7):1750-1759 or Howley et al, U.S. Pat. No. 4,419,446).

Many strains of yeast cells known to those skilled in the art are also available as host cells for expression of the polypeptides of the present invention. Other fungal cells are also employed as expression systems. Alternatively, insect cells such as *Spodoptera frugipedera* (Sf9) cells may be used.

B. Membrane-Permeabilizing Agents ("Agents")

A number of molecular entities, or environmental conditions, are known that affect the permeability of cell membranes and, under appropriate conditions, could disrupt the integrity of the cell's membrane without completely lysing the cell membrane. A list of membrane-permeabilizing agents useful in the invention includes, without limitation, bacterial protein toxins and their variants known to interact with cellular membranes (e.g., Diphtheria toxin, the Anthrax Protective Antigen, *Pseudomonas aeruginosa* exotoxin A, Botulinum toxin, Tetanus toxin, Cholera toxin, *S. aureus* α-toxin, β-barrel pore forming toxins, *E. coli* hemolysin, *Clostridium perfringens* iota toxin, listeriolysin O, cytolysins); plant protein toxins and their variants known to interact with cellular membranes (e.g., Ricin, Abrin, Modeccin); channel proteins (e.g., ion channels, voltage-regulated channels, chemically regulated channels, unregulated channels); passive transport proteins; small pore forming molecules including peptides (e.g., nystatin, amphotericin B, gramicidin A, alamethicin); enzymes (e.g., lipase); gap junction proteins; nuclear pore complexes; pore forming proteins (e.g., Porins) and holins; Colicins (e.g., Colicin E1, Colicin E3, Colicin A, Colicin Ia, Colicin Y); Protegrins; complement and complement-related proteins (e.g., perforin); membrane-fusing viral proteins (e.g., hemagglutinin); Bcl-2 proteins; detergents including SDS, Triton-X, CHAPS, deoxycholic acid, n-octyl-B-D-glupyranoside, TWEEN and Triton-X; ionophores; osmotic stress reagents including glycerol, polyethylene glycol, and dextran; variants of peptides, polypeptides, and proteins previously listed. By "variant" it is meant a nucleic acid, peptide, polypeptide, or protein which has changes in the amino acid or nucleic acid sequence, whether they are deletions, insertions, additions, or substitutions of nucleic or amino acids, as compared to an unmodified "precursor" or "parent" nucleic acid, peptide, polypeptide, or protein. The unmodified precursor or parent can be a naturally-occurring or wild-type nucleic acid, peptide, polypeptide, or protein, or a variant nucleic acid, peptide, polypeptide, or protein. The sequence of the modified protein is "derived" from the precursor or parent sequence by the substitution, deletion or insertion of one or more nucleic or amino acids of the parent sequence.

Diphtheria toxin (DT) and certain molecular variants thereof are proteins capable of forming condition-dependent pores in cellular membranes. The DT protein contains 3 structural domains: the catalytic (C), the translocation (T), and the receptor-binding (R) domains. When the DT protein is bound through the R domain to adherent mammalian cells in culture (e.g., monkey cells, Chinese hamster cells) that are subsequently exposed to a mildly acidic environment (ca. pH 4-5.5) the protein undergoes a conformational change exposing latent amino acid sequences in the T domain that insert into the proximate cell membrane. Membrane insertion of the T domain disrupts the integrity of the cell's membrane sufficiently to allow the C domain to cross the cell membrane and enter the cell's interior. The level of membrane disruption is dependent on both the concentration of DT used and the exposure pH. At appropriate concentrations of DT, membrane insertion and disruption does not lyse the cells.

In one embodiment of the invention, the membrane-permeabilizing agent is Diphtheria toxin. In another embodiment, the membrane-permeabilizing agent is an attenuated Diphtheria toxin. In another embodiment of the invention, the membrane-permeabilizing agent is DT-E148S. DT-E148S is a hypotoxic variant of Diphtheria toxin (DT) containing an approximately 500-fold attenuation of activity in the C domain. When cloned with a leader sequence, in *E. coli* the protein is secreted to the periplasmic space. When such cells are exposed to an acidic environment (ca. pH 4-6.5) the pH of the periplasmic space is reduced and portions of the periplasmic DT-E148S protein insert into the *E. coli* cell membrane. This insertion disrupts a number of functions of the inner membrane including active transport, membrane potential, and ion impermeability. The disruption of membrane function demonstrates the loss of cell membrane integrity, yet microscopic observation demonstrates the cells have not lysed but are still intact. Furthermore, the cells retain large molecules such as cytoplasmic enzymes but the cells do become freely permeable to small ultraviolet light-absorbing molecules.

Variants of DT toxin useful in the methods described herein are described in the literature. Some of these variants useful in the invention include, without limitation, C domain variants including E148D, E148Q, E148S which decrease catalytic activity and are described in Wilson et al., Biochemistry 29: p. 8643-8651 (1990). Variants which alter glutamic acid at position 148 are particularly desirable. Other variants useful in the methods of the invention include H21A, H21D, H21L, H21Q, H21R which decrease catalytic activity and are described in Blanke et al, Biochemistry 33: p. 5155-5161 (1994). Still other DT variants include those in which residues 148, 148-147, 148-146, 148-145, or 148-144 are deleted, resulting in decreased catalytic activity. See, Killeen et al, PNAS 89: p. 6207-6209 (1992). Still other DT variants include R domain variants including S508F and S525F which decrease the binding of the toxin and therefore decrease its toxicity as described in Greenfield et al, Science 274, p. 209-219 (1987). Still other variants include K516A and F530A which reduce receptor binding as described by Shen et al, Journal of Biological Chemistry 269: p. 29077-29084 (1994). Still other variants include DT with mutations and/or deletions in one or more of the following residues: S381, H384, H391, R462, D465, D467, S506, D507, Q515, K516, D519, K526, A430, L433, I464, V468, F470, L512, N524, F530, S508, S528, and S505 as described in Louie et al, Molecular Cell 1: p. 67-78 (1997). Still other variants include T domain variants including a DT fragment including amino acids 202-378, which is further described in Zhan et al, Biochemistry 34: p. 4856-4863 (1995). Still other variants useful in the invention include variants of DT referred to as cross-reacting materials (CRMs) (cross reactivity being defined as immune-cross reactivity). CRMs useful in the invention include, without limitation, CRM197 which contains a G52E mutation that renders it hypotoxic; and CRM 45 which is a truncation mutant of DT that lacks the R domain but has the T domain and is capable of disrupting membranes. Other variants useful in the invention include DT variants that lack the R domain.

In one embodiment in which the membrane permeabilizing agent is expressed by the host cell, the agent is preferably a protein. Alternatively in another embodiment in which the agent is applied externally, the membrane permeablilizing agent is a non-proteinaceous compound. In one embodiment, a membrane permeabilizing agent which may be expressed by the host cell may alternatively be supplied externally. For example, the membrane permeabilizing agent DT may be externally supplied to mammalian cells. In such cases the amount of DT applied will depend on the host cell line and the pH. For instance, more DT would be supplied at a higher pH, but less DT would be required at lower pH values. In one embodiment, $10^{-6}$ to $10^{-9}$ molar DT would be supplied. In one embodiment, for microbial host cells, such as *E. coil* and yeast, it is desirable to remove partially or completely, the host's cell wall using standard enzymatic and chemical procedures to produce spheroplasts, which can be osmotically stabilized. The external membrane permeabilizing agent, e.g., DT is then applied. In one embodiment, DT is applied at a concentration of $10^{-4}$ to $10^{-8}$ molar. In another embodiment, the membrane-permeabilizing agent is a colicin and the agent is applied to *E. coli* at a concentration of $10^{-6}$ to $10^{-9}$ molar.

C. Small Molecular Weight Compounds

The result of the permeabilizing action of the co-expressed or externally applied permeabilizing agent in these methods is that certain small molecular weight molecules can now transport freely across the cell membrane. Such small molecular weight compounds range in size between about 50 to about 2000 Daltons. In one embodiment, the small molecular weight compounds range in size between about 75 to about 2000 Daltons. In one embodiment, the small molecular weight compounds range in size between about 100 to about 2000 Daltons. In one embodiment, the small molecular weight compounds range in size between about 150 to about 2000 Daltons. In one embodiment, the small molecular weight compounds range in size between about 200 to about 2000 Daltons. In one embodiment, the small molecular weight compounds range in size between about 250 to about 2000 Daltons. In one embodiment, the small molecular weight compounds range in size between about 350 to about 2000 Daltons. In one embodiment, the small molecular weight compounds range in size between about 450 to about 2000 Daltons. In one embodiment, the small molecular weight compounds range in size between about 550 to about 2000 Daltons. In one embodiment, the small molecular weight compounds range in size between about 650 to about 2000 Daltons. In one embodiment, the small molecular weight compounds range in size between about 50 to about 1750 Daltons. In one embodiment, the small molecular weight compounds range in size between about 50 to about 1500 Daltons. In one embodiment, the small molecular weight compounds range in size between about 50 to about 1250 Daltons. In one embodiment, the small molecular weight compounds range in size between about 50 to about 1000 Daltons. In one embodiment compound that can pass through the permeabilized cell membrane is about 30, 40, 50, 60, 70, 80, 90, 100, 110, 120, 130, 140, 150, 175, 200, 225, 250, 300, 350, 400, 450, 500, 550, 600, 700, 800, 900, 1000, 1100, 1200, 1300, 1400, 1500, 1600, 1700, 1800, 1900, 2000, 2100, 2200, 2300, 2400 or 2500 Daltons.

D. Macromolecules

Macromolecules which may be produced using the expression system of the invention include, without limitation, peptides including polypeptides and proteins, DNA and RNA. The function of the macromolecule of interest is not limited by the present method. Proteins useful in the invention include, without limitation, bioactive molecules such as curative agents for diseases (e.g., insulin, interferon, interleukins, peptide hormones, anti-angiogenic peptides); peptides that bind to and affect defined cellular targets such as receptors, channels, lipids, cytosolic proteins, and membrane proteins; and peptides having an affinity for a particular material (e.g., biological tissues, biological molecules), etc. Nucleic acids which may be expressed using the method of the invention include, without limitation, DNA, RNA, antisense DNA, mRNA, tRNA, rRNA, tmRNA, siRNA, miRNA, antisense RNA, nRNA, snRAN, snoRNA and dsRNA.

Other useful macromolecules of the invention include therapeutic products. These include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophies NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful macromolecules include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful macromolecules also include complement regulatory proteins such as complement regulatory proteins, membrane cofactor protein (MCP), decay accelerating factor (DAF), CR1, CF2 and CD59.

Still other useful macromolecules include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful macromolecules include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful macromolecules include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)). Still other useful macromolecules include those used for treatment of hemophilia, including hemophilia B (including Factor IX) and hemophilia A (including Factor VIII and its variants, such as the light chain and heavy chain of the heterodimer and the B-deleted domain).

Nucleic acid sequences coding for any of the above-described proteins can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, *Nature* 292:757 (1981); Nambari et al, *Science*, 223:1299 (1984); and Jay et al, *J. Biol. Chem.* 259:6311 (1984).

Other useful macromolecules include non-naturally occurring polypeptides, such as chimeric or hybrid polypeptides having a non-naturally occurring amino acid sequence containing insertions, deletions or amino acid substitutions. Other types of non-naturally occurring gene sequences include antisense molecules and catalytic nucleic acids, such as ribozymes, which could be used to reduce overexpression of a target.

Suitable macromolecules may be readily selected by one of skill in the art.

E. Assembly of the Nucleic Acid Sequences, Molecules or Transport Vectors

For use in the methods described herein, one or both of the selected macromolecule and the membrane-permeabilizing agent are infected, transformed or transfected into the selected host cell as a nucleic acid sequence or molecule. For example, in one method a first nucleic acid sequence encodes a membrane-permeabilizing agent under the operative control of a first regulatory sequence that directs expression of the agent in the host cell. In another embodiment, a nucleic acid sequence (which may be referred to as a second nucleic acid sequence or molecule depending upon which method is employed) encodes the macromolecule under the operative control of a regulatory sequence (or second regulatory sequence) comprising a tightly regulated promoter, the regulatory sequence directing the expression of the macromolecule in the host cell.

The nucleic acid sequence encoding the macromolecule or cell permeablizing agent is cloned into an appropriate expression vector using techniques that are well known in the art. See, e.g., Sambrook, cited above. As used herein, the terms "plasmid", "vector", "transport vector" and "expression vector" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Such vectors are selected from among conventional vector types known in the art including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. In one embodiment of the invention, the first nucleic acid sequence or the second nucleic acid sequence is present independently in a transport vector, which is a plasmid, a bacteriophage or a virus. In a preferred embodiment, the vector is a plasmid with a selectable marker, e.g., an antibiotic resistance gene. See, Sambrook et al, cited above; Miller et al, 1986 Genetic Engineering, 8:277-298 and references cited therein.

In the first method of the invention, which involves the insertion of a nucleic acid sequence encoding the macromolecule and a nucleic acid sequence encoding the agent, it may be necessary to utilize plasmids containing separate selectable markers. By utilizing a first selectable marker in the first plasmid, the transformed/tranfected cells may be cultured or plated on medium containing the selection agent. In one embodiment, the selection agent is an antibiotic or antifungal. In another embodiment, a second selectable marker is included on the second plasmid. By utilizing a second selection agent, it is possible to select host cells containing both plasmids. The final result is a host cell containing two DNA segments: one segment encodes the protein acting as the membrane-permeabilizing agent and the second segment encodes the desired macromolecule for production.

The plasmid vector also includes regulatory sequences that direct expression of the agent or macromolecule in the host cell. In some embodiments of the invention, the plasmids (or other vectors carrying the sequences encoding the macromolecule or agent) include sequences permitting replication of the minigene in eukaryotes and/or prokaryotes and selection markers for these systems. These include conventional control elements which are operably linked to sequences encoding the agent or macromolecule in a manner which permits its transcription, translation and/or expression in a cell transformed or transfected with the plasmid vector. In one embodiment, the first plasmid includes a nucleic acid sequence encoding a membrane-permeabilizing agent under the operative control of a regulatory sequence that directs expression of the agent in the host cell. As used herein, "operative control" means that a nucleic acid sequence is situated in such a way with expression control, or regulatory sequences, such that the regulatory sequences direct expression of the nucleic acid sequence of interest. Regulatory sequences may be contiguous with the nucleic acid of interest or the regulatory sequences may be in trans or at a distance to control the nucleic acid of interest.

In another embodiment, the first or second plasmid includes a nucleic acid sequence encoding the macromolecule under the operative control of a second regulatory sequence comprising an inducible promoter, the regulatory sequence directing the expression of the macromolecule in the host cell. In yet another embodiment, the inducible promoter is a tightly regulated promoter.

Regulatory sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Regulatory sequences useful in the invention include any promoter capable of driving expression of the sequences of macromolecule of interest and, in the case of co-expression, the membrane-permeabilizing agent. This includes, but is not limited to: viral promoters, bacterial promoters, plant promoters, synthetic promoters, constitutive promoters, tissue specific promoters, developmental specific promoters, inducible promoters, lightly regulated promoters, tightly regulated promoters, and pathogenesis or disease related promoters. A number of such useful promoters may be found in conventional texts on recombinant protein expression or a variety of known scientific publications. Lists of suitable promoters and enhancers, selectable marker genes, origin of replication, amplicons, and other conventional components of plasmid vectors may be found in such publications as, e.g., Sambrook, cited above, and others, incorporated by reference herein.

In certain embodiments of the invention, the promoter of the first plasmid is a "leaky" promoter, e.g., an inducible promoter that exhibits variable levels of expression in the absence of the inducing agent or condition. In other embodiments of the invention, the first regulatory sequence comprises a constitutive promoter. In other embodiments of the invention, the first regulatory sequence comprises an inducible promoter. In another embodiment of the invention, the second regulatory sequence comprises a promoter different from that of the first regulatory sequence. In one embodiment, the second regulatory sequence comprises an inducible promoter different from that of the first regulatory sequence. In some embodiments of the invention, the expression of the agent is low to prevent unwanted cell toxicity or lysis.

In one embodiment, the promoter of the first plasmid is a constitutive promoter, e.g., a promoter that causes a gene to be expressed in most cell types at most times, so that the host cell transformed with this plasmid is continually producing the plasmid components. For example, certain constitutive promoters that are useful in the plasmid expressing the macromolecule include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

In certain embodiments of the invention, the promoter of the first or second, or both, plasmid(s) may be inducible or regulatable, e.g., causes expression of the nucleic acid sequence following exposure or treatment of the cell with an agent, biological molecule, chemical, ligand, light, or some other stimulus. Inducible promoters and inducible systems are available from a variety of commercial sources, including, without limitation, Invitrogen, Clontech and Ariad. Many other systems have been described and can be readily selected by one of skill in the art. A non-limiting list of such inducible promoters include the PR 1-α promoter, prokaryotic repressor-operator systems, and higher eukaryotic transcription activation systems, such as described in detail in U.S. Pat. No. 7,091,038. Such promoters include the tetracycline ("Tet") and lactose ("Lac") repressor-operator systems from *E. coli*. Other inducible promoters include the drought-inducible promoter of maize; the cold, drought, and high salt inducible promoter from potato, the senescence inducible promoter of *Arabidopsis*, SAG 12, and the embryogenesis related promoters of LEC1, LEC2, FUS3, AtSERK1, and AGI5, all known to those of skill in the art. Still other inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA*, 93:3346-3351 (1996)], the tetracycline-repressible system [Golsen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)]. Other systems include the FK506 dimer, VP16 or p65 using castradiol, diphenol murislerone, the RU486-inducible system [Wang et al, *Nat. Biotech.*, 15:239-243 (1997) and Wang at al, *Gene Ther.*, 4:432-441 (1997)] and the rapamycin-inducible system [Magari et al, *J. Clin. Invest.*, 100:2865-2872 (1997)]. Still other promoters include the rhaT promoter (Giacalone et al, *BioTechniques*, 40(3):355-63 (2006). A tightly regulated promoter is an inducible promoter which does not allow any detectable expression in the absence of the inducing agent or condition or is able to be repressed using a second reagent or condition. In one embodiment, the regulatory sequence operably linked to the nucleic acid sequence encoding the macromolecule is a tightly regulated promoter.

In a further embodiment of the invention, the vector or plasmid containing the selected nucleic acid sequence is delivered to the host cell by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. In one embodiment, the plasmid(s) containing the nucleic acid sequence encoding the macromolecule or agent are transferred to the host cell using chloride salts of metal cations such as calcium, rubidium or magnesium. In another embodiment, the plasmid(s) containing the nucleic acid sequence encoding the macromolecule or agent are transferred to the host cell using electroporation.

F. Culturing the Transfected Host Cell

One advantage of the present invention is that it is scaleable and capable of producing large quantities of recombinant macromolecule. According to the present methods, the host cells are grown to high cell densities by conventional means prior to treatment externally with, or induction or activation of intracellularly-produced, membrane-permeabilizing agent. Thus, sufficient quantities of recombinant macromolecules are obtained by adjusting the cell density of the host cell.

In either embodiment of the methods described herein, the host cell containing one or both of the nucleic acid sequences or molecules described above is cultured to a desired cell density sufficient to meet the desired production levels of the macromolecule. In one embodiment, the cell density is that considered suitable for production of the macromolecule corresponds to an $OD_{595}$ of 0.3 to 100. In one embodiment, the cell density is that considered suitable for production of the macromolecule corresponds to an $OD_{95}$ of 0.3 to 3.0. In one embodiment, the cell density is that considered suitable for production of the macromolecule corresponds to an $OD_{595}$ of 20 to 100. In one embodiment, the cell density that is considered suitable for production of the macromolecule corresponds to an $OD_{595}$ of 50-100. In one embodiment, the cell density that is considered suitable for production of the macromolecule corresponds to an $OD_{595}$ of 75-100. In one embodiment, the $OD_{595}$ is 0.3. In one embodiment, the $OD_{595}$ is 0.4. In one embodiment, the $OD_{595}$ is 0.5. In one embodiment, the $OD_{595}$ is 0.6. In one embodiment, the $OD_{595}$ is 0.7. In one embodiment, the $OD_{595}$ is 0.8. In one embodiment, the $OD_{595}$ is 0.9. In one embodiment, the $OD_{595}$ is 1.0. In one embodiment, the $OD_{595}$ is 2.0. In one embodiment, the $OD_{595}$ is 3.0. In one embodiment, the $OD_{595}$ is 4.0. In one embodiment, the $OD_{595}$ is 5.0. In one embodiment, the $OD_{595}$ is 6.0. In one embodiment, the $OD_{595}$ is 7.0. In one embodiment, the $OD_{595}$ is at least 20. In one embodiment, the $OD_{595}$ is 30. In one embodiment, the $OD_{595}$ is 40. In one embodiment, the $OD_{595}$ is 50. In one embodiment, the $OD_{595}$ is 60. In one embodiment, the $OD_{595}$ is 70. In one embodiment, the $OD_{595}$ is 80. In one embodiment, the $OD_{595}$ is 90. In one embodiment, the $OD_{595}$ is 100. In some embodiments, the cells are harvested during exponential growth phase, to ensure optimum metabolic function when the cell membrane's are permeabilized.

In any of the methods, the culture conditions are dependent upon the type of host cell being used and can readily be determined by one skilled in the art. For example, in one embodiment, when the host cell is *E. coli*, the cells are optimally grown at 37° C. in Luria Bertrani broth. In some embodiments, it may be desirous to grow the cells at room temperature. In some embodiments, the cells are grown at large scale, e.g., in a fermenter. In another embodiment, when the host cells are human HEK293 cells, the cells are optimally grown in Dulbecco's Modification of Eagle's Medium (DMEM) at 37° C. with 5% $CO_2$. The time of incubation may be readily determined by one of skill in the art. In one embodiment, the cells are cultured overnight, e.g., from 8-14 hours.

During this culturing step, it is desired that the macromolecule, preferably under the control of a tightly regulated promoter, is not expressed to detectable levels. This culture step permits accumulation of the permeabilizing agent in proximity to the cell membrane. For example, in bacterial host cells, this culturing step permits accumulation of the agent in the periplasmic space.

In one embodiment of these methods, the host cells, once cultured to a desired density, may be concentrated or harvested prior to any inducing environmental condition and culturing the cells in the presence of the nutrient cocktail. Techniques for harvesting cells are well known in the art. Briefly, in one embodiment, after the transformed cells have been plated on agar plates containing an appropriate selection antibiotic, a single colony is selected and grown overnight in appropriate medium. The broth is then poured into a plastic centrifuge bottle and spun at 5,000 rpm for 15 minutes to pellet the cells. The supernatant is then poured off. The cells are then resuspended in a desired amount of medium or buffer. In another embodiment, the transformed mammalian cells are seeded in an appropriately sized flask. The cells are grown at the desired temperature, e.g., 37° C., in an appropriate medium and allowed to come to the desired level of confluency. In the case of adherent cells, the media is then aspirated and the cells are detached from the flask with or without the use of trypsin and resuspended in the desired volume of media. In the case of suspension cells, the media containing the cells is spun down, and the pelleted cells are resuspended in an appropriate volume of media or buffer.

G. Environmental Conditions That Trigger the Permeabilizing Activity

In one embodiment of the method, the host cell at the desired density, or optionally spun down and concentrated by removal of broth, is exposed to an environmental condition that induces the membrane permeabilizing agent to disrupt the integrity of the cell membrane without complete lysis of the cell membrane. This disruption allows transport through the membrane of small molecular weight compounds. The membrane-permeabilizing agent must not lyse the host cells, but instead renders the host cell's membrane selective only for size, i.e., the membrane remains a barrier for large molecules, e.g., enzymes, but a diversity of small molecular weight compounds can readily move into the host cell.

In one embodiment of the method, in which the membrane permeabilizing agent is encoded by a plasmid contained within the cell, environmental conditions are altered to trigger the permeabilizing activity of the agent that has accumulated within the host cell. In another embodiment, in which only the plasmid controlling expression of the macromolecule is carried by the host cell, the environmental condition includes contacting the host cell with an externally applied permeabilizing agent with optionally additional environmental conditions.

According to the production methods described herein, the environmental conditions that trigger the permeabilizing activity of the permeabilizing agent include at least one of the following conditions: altering the pH, altering salt concentration, altering osmotic pressure, altering the temperature, exposing the host cell to light, and exposing the host cell to an agent, biological molecule, chemical, or ligand.

In one embodiment of the methods described herein, altering the pH comprises lowering the pH to about 4 to 6.5. In one embodiment, the pH is lowered from the neutral pH of the culturing step to the lower pH. For example, in one embodiment, the pH is lowered to about 4.

In another embodiment, the pH is lowered to about 4.5. In another embodiment, the pH is lowered to about 5.0. In another embodiment, the pH is lowered to about 5.5. In another embodiment, the pH is lowered to about 6.0. In another embodiment, the pH is lowered to about 6.5. Still other pH values intermediate between 4 and 6.5 may be selected as the environmental condition in this step.

In another embodiment of the methods described herein, the agent, biological molecule, chemical or ligand that causes the environmental condition includes without limitation, a reducing agent, an oxidizing agent, an acid, a base, or a salt. Examples of reducing agents which may be used in the invention include, without limitation, NADH, acetaldehyde, beta-mercaptoethanol and dithiothreitol. Examples of oxidizing agents which may be used in the invention include, without limitation, $NAD^+$, $H_2O_2$, and $MnO^-$. Examples of acids which may be used in the invention include, without limitation, acetic acid, hydrochloric acid, sulfuric acid, etc.

In another embodiment, the agent, biological molecule, chemical or ligand that causes the environmental condition includes a chaotrope. Examples of chaotropic agents which may be useful in the invention, include, without limitation, urea, thiourea, guanidinium chloride, and lithium perchlorate.

In another embodiment, the agent, biological molecule, chemical or ligand that causes the environmental condition includes a surfactant. Examples of surfactants which may be useful in the invention, include, without limitation, polysorbates, sorbitan esters, poloxamer, or sodium lauryl sulfate.

In another embodiment, the agent, biological molecule, chemical or ligand that causes the environmental condition includes an agent that induces the inducible promoter of the first regulatory sequence, if the membrane permeabilizing agent is under the control of an inducible promoter within the host cell. The agent that induces the inducible promoter is specific to the selected promoter. The selection of the inducing agent is well within the skill of the art. Inducing agents which may be used in the current invention, include, without limitation, IPTG, alcohol, tetracycline, steroids, metal and other compounds.

In the embodiment of the method in which the host cell does not express the permeabilizing agent, the environmental conditions further include exposing the host cell to a membrane permeabilizing agent, such as those described above. The other environmental conditions or agents causing same as itemized above, may optionally be contacted with the host cells at the same time as the permeabilizing agent or within a short time, e.g., 5 to 30 minutes, after the permeabilizing agent has been applied.

In some embodiments, it may be desired to optimize the amount, concentration, or activity of the membrane permeabilizing agent. The effectiveness of the membrane-permeabilizing agent may be assessed by examining membrane function. In one embodiment, this is accomplished by examining Proline transport, membrane potential, or $^{86}Rb$ efflux. A reduction in Proline transport, membrane potential, or $^{86}Rb$ retention of about 95% indicates that the membrane has been permeabilized. The determination of the level of permeabilization may include assessment of the amount of macromolecular production, e.g., as described in detail in Example 4.

H. Nutrient Cocktail

Once the integrity of the cell's membrane is disrupted by the performance of the methods described above, the normal metabolic activities of the host cell are compromised. With the permeability barrier of the host cell's membrane compromised by the membrane-permeabilizing agent, the host cell's interior environment will equilibrate with the host cell's external environment. As such, the methods involve supplementing the milieu of the host cell with a cocktail of nutrients to alter the interior of the host cell to create an intracellular environment that is conducive to producing the specific macromolecule of interest. The methods involve controlling the internal environment of the cell by adjusting the external environment of the cell. The cocktail includes nutrients required for the host cell to carry out the required metabolic reactions to produce the desired macromolecule.

Thus, in all embodiments of the methods described herein, the host cell, once its cell membrane has been permeabilized as described above, is cultured in the presence of a nutrient cocktail comprising components that can transport through the disrupted cell membrane. These components include an inducing agent that induces the promoter of the second regulatory sequence and other metabolic requirements that permit expression of the macromolecule in the membrane-disrupted host cell. In one embodiment, the nutrient cocktail comprises a completely defined medium, with the concentration and identity of each component specifically chosen. In another embodiment, the nutrient cocktail comprises a standard medium (e.g., LB broth) supplemented with desired components (e.g., nucleotides). One of skill in the art can determine the appropriate cocktail based on the specific conditions desired.

In one embodiment, the nutrient cocktail is at a specific pH of between pH 4-10 and salt concentration of about 10 to 500 mM. In some embodiments, the salt concentration is about 50 to 150 mM, including concentration values therebetween). In some embodiments, the pH is about 7.0 to 7.5, including pH values therebetween.

The nutrient cocktails employed in the herein-described methods comprise one or more components that can be transported through the permeabilized cell membrane to supply the cell with the components and conditions necessary for expression of the encoded macromolecule.

In one embodiment, one essential component of the cocktail is an inducing agent to induce the promoter (e.g., L-rhamnose to induce the rhaT promoter) that controls expression of the macromolecule. Surfactants may be added to increase the permeability of the membrane. Still other components include without limitation, salts, a chemical energy source, e.g., adenosine triphosphate (ATP), stabilizers, amino acids, ribonucleotides, co-factors, deoxyribonucleotides, and unnatural amino acids. Still other small molecules or environmental factors necessary to produce the macromolecule include, without limitation, osmolytes including trimethylamine N-oxide (TMAO), dimethylsulfoniopropionate, trimethylglycine, sarcosine; and redox altering reagents such as oxidized and reduced glutathione. One of skill in the art may readily select other small molecule components for the nutrient cocktail depending upon the identity of the host cell, macromolecule, and other conditions of the culture.

In some embodiments, the concentration of the osmolyte(s) and/or stabilizers in the nutrient cocktail ranges from 0.1 mM to 1M. In other embodiments, the concentration of the osmolyte(s) and/or stabilizers in the nutrient cocktail ranges from 1 mM to 1M. In other embodiments, the concentration of the salts, chemical energy source, e.g., adenosine triphosphate (ATP), stabilizers, amino acids, ribonucleotides, co-factors, deoxyribonucleotides, and/or inducing agent in the cocktail ranges from 0.1 nM to 1 mM. In still other embodiments, the concentration of these components ranges from 1 nM to 0.5 mM. In one embodiment, the concentration is 1 nM.

Once the nutrient cocktail is provided to the permeabilized host cells, the cells are, in one embodiment, cultured or held at a suitable temperature, usually between 20-40° C., for a sufficient time period to permit the cell to metabolize the macromolecule. In one embodiment, a sufficient time is overnight, or e.g., about 8 hours. Other suitable time periods include 1 to 4 hours, 5-10 hours, 12-24 hours or longer. According to these methods, the macromolecule is thereby expressed in the host cell.

Still other embodiments of either method can employ conventional steps to recover the expressed macromolecule from the host cell. Techniques for recovering the expressed macromolecule are well known in the art and include gel electrophoresis, ion-exchange chromatography, size-exclusion chromatography, reversed-phase HPLC, affinity and immunoaffinity chromatography, and metal chelate affinity chromatography. See, e.g., Sambrook, Molecular Cloning, 3$^{rd}$ Ed. (2001) and Simpson et al (Eds), Basic Methods in Protein Purification and Analysis: A Laboratory Manual (2008). With regard to polypeptides and proteins, many expression systems are available which "tag" the expressed protein to allow for ease of purification using various techniques. Affinity tags are appended to proteins so that they can be purified from their crude biological source using an affinity technique. Chromatography tags are used to alter chromatographic properties of the protein to afford different resolution across a particular separation technique. Epitope tags are short peptide sequences which are chosen because high-affinity antibodies can be reliably produced in many different species. These are usually derived from viral genes, which explain their high immunoreactivity. These tags are particularly useful for western blotting and immunoprecipitation experiments, although they also find use in antibody purification to allow purification using affinity chromatography. Specific protein tagging systems useful in the invention include, without limitation, polyhistidine-tag (HIS), Calmodulin Binding Protein (CBP), CYD (covalent yet dissociable NorpD peptide), Strep II, FLAG, HPC (heavy chain of protein C) peptide tags, glutathione-S-transferase (GST), chitin binding protein (CBP), and maltose binding protein (MBP) systems. Epitope tags include V5-tag, c-myc-tag, and HA-tag. One of skill in the art can readily select the appropriate macromolecule recovery method.

Given the teachings described herein, one of skill in the art can readily adjust the concentration and amounts of all reagents used in the method, as well as adjust the time and temperature conditions to achieve to optimize the production of the macromolecule, based on the selection of the macromolecule and cell permeablizing agent. Based upon the selection of the host cell, macromolecule and permeabilizing agent, given the teachings of this invention, one of skill in the art can optimize the culture conditions, selection of nutrient cocktail components, selection of environmental conditions, amounts and concentrations of the components used in the method, and other parameters of the method using the knowledge of the art. For example, one can readily determine optimal permeablility for any selected system using the assays described in Example 4.

As shown above, the present invention provides several advantages over known expression systems. Unlike the conventional cell-free expression systems, the presently described methods do not require a second system to prepare DNA templates (where the macromolecule is a protein or polypeptide) since the template is replicated during host cell growth. In addition, there is no loss in the capacity to produce macromolecules in the present invention during storage since cryopreservation of host cells for long periods of time is a well established art. Another advantage of the present invention is that it is scaleable and capable of producing large quantities of recombinant macromolecule. Host cell systems can be grown to high cell densities by conventional means prior to treatment with the membrane-permeabilizing agent. Thus, sufficient quantities of recombinant macromolecules can be obtained by adjusting the cell density of the host cell. Further, because the cells can be concentrated before induction of the macromolecule, the amount of reagents used may be greatly reduced.

The methods described herein create conditions inside the host cell that are conducive to the recombinant macromolecule obtaining its correct structure. The internal environment of the cell can be controlled by adjusting the external environment of the cell. With the permeability barrier of the host cell's membrane compromised by the membrane-permeabilizing agent, the host cell's interior environment will equilibrate with the host cell's external environment. Thus, the host cell's internal pH, osmolarity, redox potential, or concentration of stabilizers can be adjusted by changing the host cell's external environment. Providing the appropriate environment enables the in situ production of macromolecules with the correct structure.

III. Drug Screening Methods

A further advantage of the present invention is that it will allow for in situ drug screening. For example, a library of appropriately-modified recombinant proteins could be produced in a host cell system using the above-described production methods. Subsequent to the production of the macromolecule within the host cells as described in the methods above, the host cells can be treated with a variety of small molecular drugs, which would pass through the compromised host cell's membrane. Such small drugs, in one embodiment, are those desired to bind to the modified recombinant macromolecule, e.g., proteins. In other embodiments of the screening methods, other small drugs are those designed to trigger some signaling event or another activity of the expressed macromolecule. Conventional methods are then used to identify those host cells that contain recombinant molecules, e.g., proteins, bound to the small drug. Other conventional methods are those designed to measure the production levels or other activity of the macromolecule, etc.

As used herein, the term "drug" can refer to pharmaceutical or non-pharmaceutical compounds or substrates which are assessed for some property associated with the production or activity of the macromolecule. For example, the macromolecule of interest can be an industrial enzyme (e.g., xylanase) or a diagnostic enzyme (e.g., DNA polymerase (PCR enzyme)). In this embodiment, a library of variants is created in E coli in search for a variant that has desirable properties. For xylanase, the substrate is a polysaccharide beta 1,4-xylan.

Thus, in one embodiment, a method for in situ drug screening includes culturing in each well of a mini-well plate host cells containing (i) a first nucleic acid sequence encoding a membrane-permeabilizing agent under the operative control of a first regulatory sequence that directs expression of the agent in the host cells; and (ii) a second nucleic acid sequence encoding the macromolecule under the operative control of a second regulatory sequence comprising an inducible promoter, the regulatory sequence directing the expression of the macromolecule in the host cell. The second nucleic acid sequence in the host cells of each well encodes a different macromolecule. The co-transformed host cells are cultured to a selected cell density that permits accumulation of the agent.

The host cells in each well are then exposed to an environmental condition suitable to induce the agent to disrupt the integrity of the cell membrane without complete lysis of the membrane, and thereby allowing transport through the membrane of small molecular weight compounds. Subsequently, the host cells in each well are cultured in the presence of a nutrient cocktail comprising components that can transport through the disrupted cell membrane, the components comprising an inducing agent that induces the promoter of the second regulatory sequence of the cells in each well; and metabolic requirements that permit expression of the macromolecule in the membrane-disrupted host cells of each well, wherein the macromolecules are expressed in the host cells of each well.

In one embodiment, each well is treated with a small molecular weight test reagent that can transport through the cell membrane before induction of the second promoter. In another embodiment, each well is treated with a small molecular weight test reagent that can transport through the cell membrane after induction of the second promoter. In another embodiment, the host cells in each well may be fully lysed by contact with a conventional lysing reagent prior to treating the cells with the test reagent. The amount of such agent may be determined by one skill in the art, but may generally be between about 0.01 micromolar (0.01 µM) to 1 mM. The purpose of adding the test reagent is to assess its impact on the production of the desired macromolecule or to determine the specific residue(s) responsible for binding of the macromolecule and the test reagent. For example, in one embodiment, the test reagent binds certain variants of a macromolecule and not others. In another embodiment, the test reagent may trigger a signal event in the culture for one macromolecule variant and not the others. The identity of the macromolecule variant that responds to (e.g., is bound by) the presence of the test reagent is thereafter determined by a conventional assay that identifies and/or quantifies the macromolecule variant produced in each well.

In still another embodiment, the in situ testing method involves similar steps to those above, except that each well contains the same host cells co-transfected by the same two plasmids, i.e., the same macromolecule is expressed in each well. As described above, the cell is permeabilized by contact with the environmental condition, and contacted with the nutrient cocktail. However, in this embodiment, each well is treated with a different test reagent, i.e., from a library of test compounds. The conventional assay is thereafter used to determine which test reagent impacted the production of the macromolecule or bound to the macromolecule in the same manner as described above.

In yet a further embodiment, the second production method may be employed in the screening assay. The host cell contains only a single plasmid with a nucleic acid sequence encoding the macromolecule (or variants of macromolecules). The cells are cultured to a desired density in each well of a multi-well plate prior to contact with the externally applied permeabilizing agent and/or environmental condition that induces the permeabilizing event. The library of test reagents (or a single test reagent) may then be applied at the same time, or sometime after, the permeabilized cells in each well are contacted with the nutrient cocktails as defined above. A conventional assay performed on the contents of each well will determine which test reagent induces a response in a single macromolecule or which variant of the macromolecule responds to single test reagent, in the manner described above.

IV. Examples

The following examples demonstrate the use of the compositions and methods of the invention.

Example 1

Method of Production of Acidic Fibroblast Growth Factor (aFGF)

A. Construction of the Host Cells Containing Two Nucleic Acid Molecules for Co-Expression of the Membrane Permeabilizing Agent and the Macromolecule DNA sequences encoding as the membrane permeabilizing agent, an intact diphtheria toxin (DT) gene containing a 3-base pair mutation in an active site residue (E148S), resulting in a hypotoxic, attenuated version of DT called DT-E148S. This nucleic acid sequence is assembled using conventional techniques and as described in O'Keefe and Collier, PNAS, 86:343-6 (1989).

This sequence is cloned into the pF1KT7-Flexi™ plasmid vector (Promega) behind an inducible T7 promoter. The T7 promoter is inducible with isopropyl β-D-thiogalactopyranoside (IPTG), but exhibits a basal level of expression (leaky expression) in the absence of IPTG. The pF1KT7-Flexi™ vector contains a selectable marker kan$^r$ (for kanamycin resistance) which allows for identification of a successfully transfected E. coli host.

This "first" plasmid containing DT-E148S (pDT-E148S) is transformed into competent E. coli host cells and streaked on LB agar containing 50 µg/ml of kanamycin and grown overnight at 37° C. A single colony is selected and grown for 15 hours at 37° C. in 15 mL LB broth containing kanamycin. The cells are pelleted and used for the next step.

A "second" plasmid, the pRHA plasmid is constructed as described in Giacalone et al, 2006, Biotechniques, 40(3):355-63. The pRHA plasmid contains a selectable marker amp$^r$ (for ampicillin resistance) which allows for identification of a successfully transfected *E. coli* host. DNA sequences encoding the macromolecule, protein aFGF, are cloned into the pRHA plasmid behind the rhaT promoter. Optionally, the protein is tagged with GST or a histidine tag for later purification from the host cells. The rhaT promoter is a tightly regulated promoter, inducible by the addition of L-rhamnose and repressed by the presence of D-glucose. This "second" plasmid comprising the nucleic acid sequence encoding the target macromolecule is transformed into *E. coli* cells containing the "first" plasmid encoding the membrane permeabilizing agent DT-E148S. The co-transformed *E. coli* host cells are streaked on LB agar containing ampicillin and kanamycin and grown overnight at 37° C. to select for cells containing both plasmids. A single colony is selected and grown for 15 hours at 37° C. in 15 mL LB broth containing ampicillin and kanamycin.

B. Culturing of the Host Cells to a Selected Density

The *E. coli* is cultured in LB broth, which is supplemented with 0.2% D-glucose to repress expression of the macromolecule, but permit expression of the DT-E148S. During this time, the *E. coli* host cell is expressing DT-E148S due to its leaky promoter and localizing it in the cell's periplasmic space due to its leader sequence. When the host cells reach a selected cell density of $OD_{595}$ of 1.0, which is the cell density generally selected to maximize production of the macromolecule, the *E. coli* host cells are harvested and the broth is poured off.

C. Permeabilizing the Host Cells

The cells are then exposed to an environmental condition that induces the permeabilizing agent to disrupt the integrity of the cell membrane without complete lysis of the cell membrane. In this experiment, the cells are resuspended in acidic buffer (sodium succinate) to lower the pH to about 5.0 for about 5 minutes. Without wishing to be bound by theory, the acidic medium induces a conformation change in the periplasmic DT-E148S molecule that allows it to insert into the cell membrane and disrupt its integrity without completely lysing the host cells. This disruption of the cell membrane thereby allows transport through the membrane of small molecular weight compounds, e.g., small molecules of about 50 to 2000 Daltons.

D. Producing the Macromolecule

After permeabilization occurs, the acidic buffer is exchanged for LB and a nutrient cocktail that includes L-rhamnose, which induces the rhaT promoter, as well as other small molecule compounds required for metabolism of the permeabilized cell and production of the protein aFGF in the membrane-disrupted cells. These molecules are of a size that can transport through the disrupted cell membrane. Such components in this case include ATP, amino acids, and ribonucleotides. Each component is added to a concentration of about 1 mM. The induced cells are kept at 37° C. overnight. The cells are pelleted and lysed and the macromolecular protein aFGF is purified using conventional chromatography methods.

Example 2

Method of Production of Fibroblast Growth Factor 20 (FGF-20)

A. Construction of Host Cells Containing a Nucleic Acid Molecule For Expression of a Macromolecule The pRHA plasmid, constructed as described in Giacalone et al, 2006, Biotechniques, 40(3):355-63, contains a selectable marker $amp^r$ (for ampicillin resistance) which allows for identification of a successfully transfected *E. coli* host. DNA sequences encoding the macromolecule, protein FGF-20, are cloned into the pRHA plasmid behind the rhaT promoter. Optionally, the protein is tagged with GST or a histidine tag for later purification from the host cells. The rhaT promoter is a tightly regulated promoter, inducible by the addition of L-rhamnose and repressed by the presence of D-glucose. This plasmid comprising the nucleic acid sequence encoding the target macromolecule is transformed into competent *E. coli* cells. The transformed *E. coli* host cells are streaked on LB agar containing 50 µg/ml ampicillin and grown overnight at 37° C. to select for cells containing the plasmid. A single colony is selected and grown for 15 hours at 37° C. in 15 mL LB broth containing ampicillin. The cells are pelleted and used for the next step.

B. Culturing of the Host Cells to a Selected Density

The *E. coli* is cultured in LB broth, which is supplemented with 0.2% D-glucose to repress expression of the macromolecule. When the host cells reach a selected cell density of $OD_{595}$ of 1.0, which is the cell density generally selected to maximize production of the macromolecule, the *E. coli* host cells are harvested and the broth is poured off.

C. Permeabilizing the Host Cells

The cells are then exposed to an externally added permeabilizing agent Colicin Y under an environmental condition sufficient to disrupt the integrity of the cell membrane without complete lysis of the cell membrane. In this experiment, the harvested *E. coli* are then resuspended in neutral buffer and treated with 2 µg/mL of the permeabilizing agent, Colicin Y, for about 5 minutes. This treatment disrupts the integrity of the cell membrane without completely lysing the host cells. This disruption of the cell membrane thereby allows transport through the membrane of small molecular weight compounds, e.g., small molecules of about 50 to 2000 Daltons.

D. Producing the Macromolecule

After permeabilization occurs, the neutral buffer is exchanged for LB and a nutrient cocktail that includes L-rhamnose, which induces the rhaT promoter, as well as other small molecule compounds required for metabolism of the permeabilized cell and production of the protein FGF-20 in the membrane-disrupted cells. These molecules are of a size that can transport through the disrupted cell membrane. Such components in this case include ATP, amino acids, and ribonucleotides, which are added at a concentration of about 1 mM. The induced cells are kept at 37° C. overnight. The cells are pelleted and lysed and the macromolecular protein FGF-20 is purified using conventional chromatography methods.

Example 3

In Situ Drug Screening

A. Construction of the Host Cells Containing Two Nucleic Acid Molecules For Co-Expression of the Membrane Permeabilizing Agent and the Macromolecule Competent *E coli* host cells are transfected with plasmid pDT-E148S as described in Example 1. Variants of protein 5-alpha reductase are obtained and cloned, separately, into a pRHA plasmid behind the rhaT promoter, as described in Example 1, providing a library of pRHA plasmids differing only in the protein 5-alpha reductase variant encoded thereby. Each plasmid containing a protein variant coding sequence is transformed into *E. coli* cells containing pDT-E148S. The transformed cells are streaked on LB agar containing ampicillin and kanamycin and grown overnight at 37° C. to select for cells containing both plasmids. A single colony of host cells carrying each variant is selected and grown for 15 hours at 37° C. in 15 mL LB broth containing ampicillin and kanamycin.

B. Culturing of the Host Cells to a Selected Density

The variant E. coli host cells are plated in a 96-well plate, each plate containing a different variant. Each E. coli in the wells is cultured in LB broth, which is supplemented with 0.2% D-glucose to repress expression of the macromolecule variant, but permit expression of the DT-E148S, which accumulates in the periplasm of the host cell. When the host cells reach a selected cell density of $OD_{595}$ of 1.0, the E. coli host cells are harvested and the broth is poured off.

C. Permeabilizing the Host Cells

The cells in each well are resuspended in acidic buffer (sodium succinate) to lower the pH to about 5.0 for about 5 minutes. Without wishing to be bound by theory, the acidic medium induces a conformation change in the periplasmic DT-E148S molecule that allows it to insert into the cell membrane and disrupt its integrity without completely lysing the host cells. This disruption of the cell membrane thereby allows transport through the membrane of small molecular weight compounds, e.g., small molecules of about 50 to 2000 Daltons.

D. Producing the Macromolecule

After permeabilization occurs, the acidic buffer in each well is exchanged for LB and a nutrient cocktail that includes L-rhamnose, which induces the rhaT promoter, as well as other small molecule compounds required for metabolism of the permeabilized cell and production of the protein 5-alpha reductase in the membrane-disrupted cells. These molecules are of a size that can transport through the disrupted cell membrane. Such components in this case include ATP, amino acids, and ribonucleotides, which are added at a concentration of about 1 mM.

Also added to each well is about 0.01 micromolar to 1 mM of a test reagent, i.e., a small molecular weight compounds, e.g., finasteride, which can also transport through the disrupted cell membrane.

The induced cells are kept at 37° C. overnight. The cells are pelleted and lysed and the macromolecular protein 5-alpha reductase is purified using a chromatography tag. If the test reagent was able to bind the variant of protein 5-alpha reductase, the test reagent will be detected by mass spectrometry. Mass spectrometry will also be used to identify the binding variant.

This drug screening method enables one of skill in the art to determine the identity of the variant macromolecule that responded to the test reagent.

In another embodiment of this experiment, the same macromolecule is expressed in each well, but each well is contacted with a different test reagent to identify which test reagent binds the macromolecule.

Example 4

Determination of Cell Permeability

For any of the above Examples, the following known and published procedures are an example of one method that may be used to test the extent of permeability of the cell membrane, after application or expression of the cell permeabilizing agent. These procedures are described in more detail in O'Keefe and Collier, PNAS, 86:343-6 (1989), among other publications. One of skill in the art may use these or similar procedures in optimizing the methods described herein.

The cells are viewed microscopically to ensure that the cells have not been lysed.

A. Membrane Potential.

Transformed *E. coli* cells are grown in L broth to an $OD_{595}$ of 1.0. Cells are spun down and resuspended in 2 mM Tris-HCl/50 mM NaCI, pH 7.0, to a concentration of $3\times10^{9}$ cells per ml. For each experimental point, the cells are diluted 1:10 into 5 mM buffer at various pH values containing 50 mM NaCl. From this point, the cells are kept at 37° C. in a thermoregulated, magnetically stirred cuvette. The following buffers are added to individual cuvettes: Pipes (pH 7.0 and 6.5), Mes (pH 6.0), and sodium citrate/sodium succinate (pH 5.5 and 5.0). The cells (containing the pH specific buffers) are incubated for 1 min and then brought to 100 mM Tris-HC1 (pH 7.5). One minute later 3,3 '-dipropylthiadicarbocyanine iodide (Molecular Probes, Eugene, Oreg.) is added to a final concentration of 1 μg/ml. The fluorescence, measured when the signal stabilized, is divided by the fluorescence at pH 7.0 to obtain relative fluorescence. Fluorescence is measured in a SLM AMINCOO®(Urbana, Ill.) SPF-500C spectrofluorometer with excitation at 645 nm and emission at 668 nm. Both slits are set at 5 nm.

B. Proline Transport.

Cells grown overnight in potassium-free M9 medium (sodium phosphate is substituted for potassium phosphate) are diluted 1:100 in the same medium. After growing for 5 hr, the cells are resuspended in growth medium to an $OD_{595}$ of 1.0. 0.1 mL of cells are added to 1.9 ml of 20 mM buffer at various pH values (same as above) containing 4.8 μCi (1 Ci=37 GBq) of L-[2,3,4,5-$^{3}$H]proline. After 10 min at 37° C., the cells are filtered through Millipore HA filters and washed with 5 ml of potassium-free M9 salts. The filters are dried and dissolved in OCS (Amersham), and the radioactivity is measured in a scintillation counter.

C. $^{86}$Rb Efflux.

Cells are grown as for the transport assays. After resuspending to an $OD_{595}$ of 1.0, the cells are incubated in the presence of $^{86}$RbCl (20 μCi/ml) for 1 hr at 37° C. 0.1 ml of cells are then added to 1.9 ml of 20 mM buffer (same as above) at various pH values and incubated for 10 min at 37° C. The cells are then filtered through Millipore HA filters presoaked in wash buffer. The filters are washed with 5 ml of M9 salts supplemented with 10 mM RbCl and dried, and radioactivity is determined in a γ counter.

D. Determination of Membrane Permeation

A reduction of >95% activity in any of the above assays indicates that the cell membrane has been permeabilized sufficiently for transport of small molecular weight compounds, without complete lysis of the membrane, according to the methods described herein.

All documents cited in the above specification are incorporated herein by reference. While the invention has been described with reference to specific embodiments and examples, it is appreciated that modifications can be made without departing from the spirit of the invention. For example, one of skill in the art may readily select, inter alia, other in situ drug screening protocols, other macromolecules, other nutrient cocktails and detection assays which use the host cells and methods of this invention to identify test reagents with desirable properties.

Such modifications are intended to fall within the scope of the appended claims.

The invention claimed is:

1. A method for recombinantly expressing a macromolecule in a host cell comprising:

a) culturing a host cell containing:
  i. a first nucleic acid sequence encoding a membrane-permeabilizing agent under the operative control of a first regulatory sequence that directs expression of the agent in the host cell; and
  ii. a second nucleic acid sequence encoding the macromolecule under the operative control of a second regulatory sequence comprising an inducible promoter, the regulatory sequence directing the expression of the macromolecule in the host cell;
to a selected cell density sufficient to meet the desired production levels of the macromolecule;
b) exposing the host cell of (a) to an environmental condition that induces the agent to disrupt the integrity of the cell membrane without complete lysis of the cell membrane, thereby cancelling the energized membrane function but allowing transport through the membrane of small molecular weight compounds; and
c) providing the cells of (b) with a nutrient cocktail comprising components that can transport through the disrupted cell membrane, the components comprising an inducing agent that induces the promoter of the second regulatory sequence, metabolic requirements that permit expression of the macromolecule in the membrane-disrupted host cell, and a chemical energy source;
wherein the macromolecule is expressed in the host cell.

2. A method for enhancing recombinant expression of a macromolecule in a host cell comprising:
  a) contacting a host cell with a membrane-permeabilizing agent that disrupts the integrity of the cell membrane without complete lysis of the membrane, cancelling the energized membrane function but allowing transport through the membrane of small molecular weight compounds, the host cell containing a nucleic acid sequence encoding a macromolecule under the operative control of a regulatory sequence comprising an inducible promoter, the regulatory sequence directing expression of the macromolecule in the host cell;
  b) providing the cells of (a) with a nutrient cocktail comprising components that can transport through the disrupted cell membrane, the components comprising metabolic requirements that permit enhanced expression of the macromolecule in the membrane-disrupted host cell including a chemical energy source.

3. The method according to claim 1, wherein the host cell is selected from the group consisting of: bacterial cells, yeast cells, mammalian cells, and insect cells.

4. The method according to claim 1, wherein the macromolecule is a protein, DNA or RNA.

5. The method according to claim 1 wherein the first nucleic acid sequence or the second nucleic acid sequence is present independently in a transport vector, which is a plasmid, a bacteriophage or a virus.

6. The method according to claim 1, wherein the first regulatory sequence comprises a constitutive promoter or an inducible promoter.

7. The method according to claim 1, wherein the second regulatory sequence comprises a promoter different from that of the first regulatory sequence.

8. The method according to claim 1, wherein the inducible promoter of the second regulatory sequence is a tightly regulated promoter.

9. The method according to claim 1, wherein the environmental condition of step (b) comprises at least one of: altering the pH, altering salt concentration, altering osmotic pressure, altering the temperature, exposing the host cell to light, and exposing the host cell to an agent, biological molecule, chemical, or ligand.

10. The method according to claim 9, wherein altering the pH comprises changing the pH to about 4 to 6.5.

11. The method according to claim 9, wherein the agent, biological molecule, chemical or ligand is selected from the group consisting of a reducing agent, an oxidizing agent, an acid, a base, a salt, a chaotrope, a surfactant, and an agent that induces the inducible promoter of the first regulatory sequence.

12. The method according to claim 1, wherein the nutrient cocktail comprises one or more components selected from the group consisting of: an inducing agent to induce the promoter that controls expression of the macromolecule, adenosine triphosphate (ATP), an amino acid, a ribonucleotide, a cofactor, a deoxyribonucleotide, an unnatural amino acid, a stabilizer, an osmolyte, a redox altering agent, and an environmental factor necessary to produce the macromolecule.

13. The method according to claim 1, further comprising recovering the expressed macromolecule from the host cell.

14. The method according to claim 1, further comprising concentrating or harvesting the host cells prior to providing the cells with the nutrient cocktail.

15. A method for in situ drug screening comprising:
  a) culturing in each well of a mini-well plate host cells containing:
    i. a first nucleic acid sequence encoding a membrane-permeabilizing agent under the operative control of a first regulatory sequence that directs expression of the agent in the host cells; and
    ii. a second nucleic acid sequence encoding the macromolecule under the operative control of a second regulatory sequence comprising an inducible promoter, the regulatory sequence directing the expression of the macromolecule in the host cell;
  to a selected cell density sufficient to meet the desired production levels of the macromolecule; wherein the second nucleic acid sequence in the host cells of each well encodes a different macromolecule;
  b) exposing the host cells of (a) to an environmental condition suitable to induce the agent to disrupt the integrity of the cell membrane without complete lysis of the membrane, cancelling the energized membrane function but allowing transport through the membrane of small molecular weight compounds;
  c) providing the host cells of (b) with a nutrient cocktail comprising components that can transport through the disrupted cell membrane, the components comprising an inducing agent that induces the promoter of the second regulatory sequence of the cells in each well; a chemical energy source; and metabolic requirements that permit expression of the macromolecule in the membrane-disrupted host cells of each well, wherein the macromolecules are expressed in the host cells of each well;
  d) treating the host cells of each well with a test reagent; and
  e) determining the identity of the macromolecule that responded to the test reagent.

16. A method for in situ drug screening comprising:
  a) culturing in each well of a mini-well plate host cells containing:
    i. a first nucleic acid sequence encoding a membrane-permeabilizing agent under the operative control of a first regulatory sequence that directs expression of the agent in the host cells; and ii. a second nucleic acid sequence encoding the macromolecule under the operative control of a second regulatory sequence comprising an inducible promoter, the regulatory sequence directing the expression of the macromolecule in the host cell;
to a selected cell density that permits accumulation of the agent;

b) exposing the host cells of (a) to an environmental condition suitable to induce the agent to disrupt the integrity of the cell membrane without complete lysis of the membrane, cancelling the energized membrane function but allowing transport through the membrane of small molecular weight compounds;

c) providing the host cells of (b) with a nutrient cocktail comprising components that can transport through the disrupted cell membrane, the components comprising an inducing agent that induces the promoter of the second regulatory sequence of the cells in each well, metabolic requirements that permit expression of the macromolecule in the membrane-disrupted host cells of each well, and a chemical energy source; wherein the macromolecules are expressed in the host cells of each well;

d) treating the host cells of each well with a different test reagent; and e) determining the identity of the test reagent that induced a response in the macromolecule.

17. The method according to claim 15, wherein the response of the cells to a test reagent is binding or triggering of a signal event.

18. The method according to claim 15, further comprising lysing the cells prior to treating the cells with a test reagent.

19. The method according to claim 15, wherein a test reagent is a small molecule that transports through the disrupted cell membranes.

* * * * *